US010195170B2

(12) United States Patent
Chen et al.

(10) Patent No.: US 10,195,170 B2
(45) Date of Patent: *Feb. 5, 2019

(54) METHODS FOR INHIBITING EXPRESSION OF ASC, EXPRESSION OF NLRP3, AND/OR FORMATION OF NLRP3 INFLAMMASOME COMPLEX USING DIACEREIN OR ITS ANALOGS

(71) Applicant: TWi Biotechnology, Inc., Taipei (TW)

(72) Inventors: Chih-Kuang Chen, Taipei (TW); Jing-Yi Lee, Taipei (TW); Wei-Shu Lu, Taipei (TW); Carl Oscar Brown, III, San Diego, CA (US)

(73) Assignee: TWI Biotechnology, Inc., Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/238,950

(22) Filed: Aug. 17, 2016

(65) Prior Publication Data
US 2017/0049733 A1 Feb. 23, 2017

Related U.S. Application Data

(60) Provisional application No. 62/206,102, filed on Aug. 17, 2015.

(51) Int. Cl.
*A61K 31/192* (2006.01)
*A61K 31/216* (2006.01)

(52) U.S. Cl.
CPC .......... *A61K 31/192* (2013.01); *A61K 31/216* (2013.01); *Y02A 50/385* (2018.01); *Y02A 50/411* (2018.01)

(58) Field of Classification Search
CPC .................. A61K 31/192; A61K 31/216
See application file for complete search history.

(56) References Cited

U.S. PATENT DOCUMENTS

2002/0128317 A1* 9/2002 Charbit ................. A61K 31/00
514/548
2010/0150938 A1* 6/2010 Latz ................... A61K 31/4025
514/1.1
2014/0199320 A1 7/2014 Jankovic et al.

FOREIGN PATENT DOCUMENTS

WO  WO 2010/003092  1/2010
WO  WO 2011/127240  10/2011

OTHER PUBLICATIONS

Nicolas et al. (Cln. Pharmacokinet (1998); 35(5): 347-359).*
Jin et al. ( Proc Natl Acad Sci Sep. 6, 2011; 108(36): 14867-14872).*
ISR and Written Opinion in corresponding Application No. PCT/US2016/047272 dated Oct. 31, 2016.
Ozaki et al., "Targeting the MLRP3 inflammasome in chronic imflammatory diseases: current perspectives", Journal of Imflammation Research, Jan. 16, 2015, pp. 15-27.

* cited by examiner

Primary Examiner — Shirley V Gembeh
(74) Attorney, Agent, or Firm — Wood, Phillips, Katz, Clark & Mortimer

(57) ABSTRACT

Methods and compositions for inhibiting expression of ASC, expression of NLRP3, and/or formation of NLRP3 inflammasome complex by using diacerein or its analogs are provided. Also provided are methods and compositions for the treatment and/or prevention of a disorder mediated by ASC and/or NLRP3, and/or by formation of NLRP3 inflammasome complex by using diacerein or its analogs.

8 Claims, 2 Drawing Sheets
(1 of 2 Drawing Sheet(s) Filed in Color)

METHODS FOR INHIBITING EXPRESSION OF ASC, EXPRESSION OF NLRP3, AND/OR FORMATION OF NLRP3 INFLAMMASOME COMPLEX USING DIACEREIN OR ITS ANALOGS

BACKGROUND OF THE INVENTION

Field of the Invention

The present invention relates to methods for inhibiting expression of ASC (apoptosis-related speck-like protein containing a caspase recruitment domain [CARD]), expression of NLRP3 (NLR family, pyrin domain containing 3), and/or formation of NLRP3 inflammasome complex. In particular, the invention relates to methods for the treatment and/or prevention of a disorder mediated by ASC and/or NLRP3, and/or by formation of NLRP3 inflammasome complex by using diacerein or its analogs. Pharmaceutical compositions comprising diacerein or its analogs are also provided.

Description of the Related Art

Nucleotide-binding oligomerization domain-like receptors (NLRs) are an evolutionarily conserved family of cytosolic receptors with a tripartite structure that share a common central nucleotide-binding and oligomerization (NACHT) domain that is usually flanked by a C-terminal leucine-rich repeat (LRR) domain and a N-terminal effector pyrin domain (PYD) or a caspase recruitment domain (CARD). Once activated by pathogen-associated molecules or damage-associated molecules, NLRs oligomerize and recruit the adaptor protein ASC and the cysteine protease procaspase-1 and form an inflammasome complex, leading to the autocatalysis and activation of caspase-1. Active caspase-1 ultimately cleaves the precursor proinflammatory cytokines pro-IL-1β and pro-IL-18 into their mature secreted forms.

The formation of inflammasome complex from NLRs has been implicated in the pathogenesis of a wide variety of diseases, including inherited autoinflammatory conditions as well as chronic diseases. In particular, it has been linked to diseases such as Alzheimer's disease atherosclerosis, metabolic syndrome, and age-related macular degeneration.

Based on the above mentioned mechanism, suppressing NLRs or ASC and the formation of inflammasome complex has been considered as a potential way to treat the diseases mediated by these proteins (Ozaki et al., *Journal of Inflammation Research* 2015, 8:15-27).

US Publication No. 2014/0199320 discloses a method for the treatment of acne through inhibition of IL-1β, NLRP3, ASC, IL-1 receptor type 1, caspase-1 or cathepsin B by numerous inhibitors including IL-1β inhibitors. However, it focuses on suppression of IL-1β, rather than NLRP3 and ASC, and thus gives little clue on which inhibitors would have direct inhibitory effect on NLRP3 and ASC.

Besides, many reagents that target IL-1β and IL-18 (the products from inflammasome activation) have been developed to treat inflammatory diseases, including anakinra (a recombinant IL-1 receptor antagonist), canakinumab (an IL-1β antibody), rilonacept (a soluble decoy IL-1 receptor), IL-18 binding, protein, soluble IL-18 receptors and anti-IL-18 receptor monoclonal antibodies, but these reagents suppress IL-1β or IL-18, not NLRP3 and ASC.

Therefore, there is still a need in the art for specific methods and compounds which are able to suppress NLRs or ASC and to inhibit the formation of inflammasome complex.

SUMMARY OF THE INVENTION

The inventors of the present invention found that diacerein and its analogs are excellent inhibitors of the expression of ASC and NLRs (especially NLRP3), and accordingly are able to decrease the formation of inflammasome complex. Therefore, diacerein and its analogs can be used for treating and/or preventing disorders mediated by ASC and/or NLRs.

The primary objective of this invention is to provide a method of inhibiting ASC expression, NLRP3 expression, and/or formation of NLRP3 inflammasome complex in a cell, comprising contacting the cell with a compound selected from the group consisting of diacerein, rhein, monoacetylrhein, salts, esters and prodrugs thereof (hereinafter referred to as "diacerein or its analogs").

Another objective of this invention is to provide a method of inhibiting ASC expression, NLRP3 expression, and/or formation of NLRP3 inflammasome complex in a subject in need thereof, comprising administering diacerein or its analogs to said subject.

Yet a further objective of this invention is to provide a method for treatment and/or prevention of a disorder mediated by ASC and/or NLRP3, and/or by formation of NLRP3 inflammasome complex in a subject in need thereof, comprising administering diacerein or its analogs to said subject.

The detailed technology and preferred embodiments implemented for this invention are described in the following paragraphs accompanying the appended drawings

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
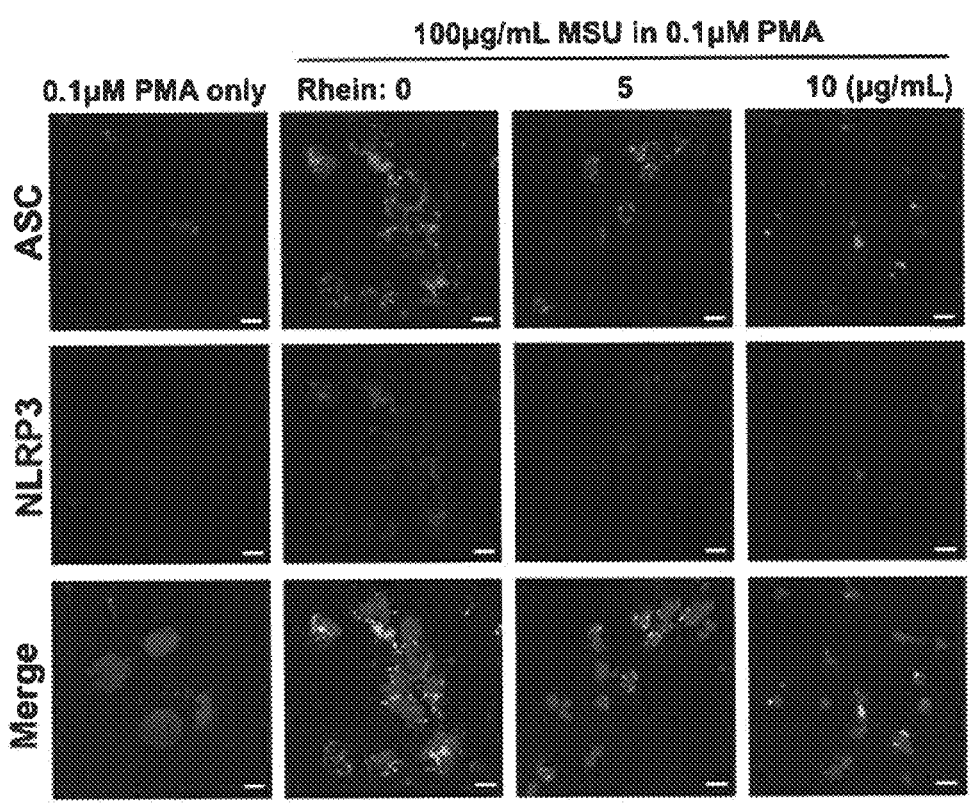
FIG. 1 shows images of ASC and NLRP3 from a fluorescence confocal microscopy after THP-1 cells were stimulated by monosodium urate (MSU) and treated with various doses of rhein.

The term "therapeutically effective amount," as used herein, refers to an amount that alleviates or reduces one or more symptoms of a disease.

The term "diacerein or its analogs," as used herein, refers to diacerein, rhein, monoacetylrhein, or a salt or ester or a prodrug thereof.

The term "prodrug," as used herein, refers to any compound that can be converted into rhein and exerts its physiological function in form of rhein within the body.

Unless otherwise stated herein, the terms "a (an)", "the" or the like used in this specification (especially in the Claims hereinafter) shall be understood to encompass both the singular form and the plural form.

Chemically, rhein is 9, 10-dihydro-4, 5-dihydroxy-9, 10-dioxo-2-anthracene carboxylic acid which has a structure of Formula (I). One of its prodrugs, diacerein, is 4, 5-bis (acetyloxy) 9, 10-dihydro-4, 5-dihydroxy-9, 10-dioxo-2- anthracenecarboxylic acid which has a structure of Formula (II). Diacerein, is entirely converted into rhein before reaching the systemic circulation, and exerts its physiological function in form of rhein within the body.

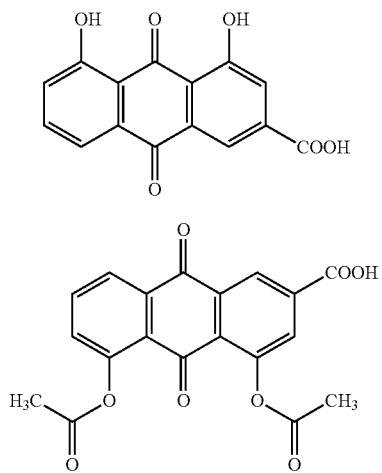

Formula (I)

Formula (II)

Diacerein is an anti-inflammatory agent widely used in the treatment of osteoarthritis, which has been demonstrated to inhibit interleukin-1 (IL-1) signaling. Presently, diacerein capsules are available in 50 mg strength and are marketed under various trade names in different countries, including Art 50®, Artrodar®, etc.

As stated above, the inventors of the present invention found that diacerein or its analogs may inhibit the expression of ASC. Thus, the invention provides a method of inhibiting ASC expression in a cell, comprising contacting the cell with a compound selected from the group consisting of diacerein, rhein, monoacetylrhein, salts, esters and prodrugs thereof.

In one embodiment, the cell in this method is a human cell.

The present invention also provides a method of inhibiting ASC expression in a subject in need thereof, comprising administering diacerein or its analogs to subject.

In one embodiment, the subject is a human.

Preferably, the ASC expression is inhibited by at least 30%, and more preferably, by at least 50% by diacerein or its analogs.

Because ASC is involved in the formation of inflammasome complexes from various NLRs, diacerein or its analogs can suppress the formation of these inflammasome complexes through decreasing the ASC expression, and can be used to treat disorders mediated by these complexes accordingly.

To date, five different inflammasome complexes have been clearly identified, i.e., NLRP1, NLRP2, NLRP3, AIM2, and IPA/NLRC4. Each inflammasome is activated in response to different stimuli. Other members of the NLR family, namely NLRP6, NLRP7 and NLRP12, have also been described to form inflammasomes with ASC leading to caspase-1 activation, although their specific ligands are still unknown.

So far, NLRP3 inflammasome complex (i.e., inflammasome formed by NLRP3, ASC and procaspase-1) is the best characterized inflammasome, which has been shown to have major implications in the development of chronic diseases.

Diacerein or its analogs were also found to inhibit NLRP3 expression. Hence, the present invention also relates to a method of inhibiting NLRP3 expression and/or the formation of NLRP3 inflammasome complex in a cell, comprising contacting the cell with diacerein or its analogs.

In one embodiment, the cell in this method is a human cell.

The present invention also relates to a method of inhibiting NLRP3 expression and/or the formation of NLRP3 inflammasome complex in a subject in need thereof, comprising administering diacerein or its analogs to said subject.

In one embodiment, the subject is a human cell.

Preferably, the NLRP3 expression is inhibited by at least 30%, and more preferably, by at least 50% by diacerein or its analogs.

The present invention further provides a method for the treatment and/or prevention of a disorder mediated by ASC and/or NLRP3 and/or the formation of NLRP3 inflammasome complex in a subject, comprising administering to the subject in need of such treatment and/or prevention a therapeutically effective amount of diacerein or its analogs. The administration causes a decrease in ASC expression and/or NLRP3 expression in the subject.

In one embodiment, the subject is a human.

In one embodiment, diacerein or its analogs are administered at a dose of about 5 to 500 mg per day.

Preferably, the disorder in this method is selected from the group consisting of gout, pseudogout, gout flare prophylaxis, obesity-induced insulin resistance, type 2 diabetes, Alzheimer's Disease (AD), age-related macular degeneration (AMD), atherosclerosis, inflammatory bowel disease (IBD), rheumatoid arthritis (RA), cancer, systemic lupus erythematosus (SLE), asthma, allergic asthma, contact hypersensitivity, sunburn, UVB-induced skin damage, essential hypertension, cryopyrin-associated periodic syndromes (CAPS), Muckle-Wells syndrome (MWS), familial cold autoinflammatory syndromes (FCAS), neonatal onset multi-systemic inflammatory disease/chronic infantile neurological cutaneous and articular syndrome (NOMD/CINCA), B-cell non-Hodgkin's lymphoma, acute myocardial infarction, myocardial infarction, allergic rhinitis, nasal polyposis, autoimmune encephalomyelitis (EAE), multiple sclerosis (MS), skin fibrosis in human systemic sclerosis (SSc), hyperhomocysteinemia (hHcys)-associated glomerular sclerosis, end-stage renal disease (ESRD), atherosclerosis, hepatic fibrosis, renal fibrosis, pulmonary fibrosis, chronic pulmonary fibrotic disorders, idiopathic pulmonary fibrosis (IPF), fibrotic lung disease, cystic fibrosis (CF), cardiac fibrosis, pancreatic islet fibrosis, chronic kidney disease (CKD), crystalline nephropathies, chronic obstructive pulmonary disease (COPD), ocular Bechet's disease, uvetitis, psoriasis, asbestosis, silicosis, malaria, Dengue, bacterial infection, allergic dermatitis, hyperoxic lung injury, conjunctivitis, keratitis, atopic dermatitis, psoriatic arthritis, vitiligo, Crohn's disease, metabolic syndromes linked with obesity, inflammation-associated cancers, hypersensitivity dermatitis, familial Mediterranean fever (FMF), familial Hibernian Fever (FHF), familial cold urticarial (FCU), pyogenic sterile arthritis, pyoderma gangrenosum, acne (PAPA), systemic onset juvenile arthritis, mevalonate kinase deficiency (MKD), Epidermolysis bullosa (EB), Epidermolytic ichthyosis (EI), and Schnitzler's syndrome (SS).

More preferably, the disorder in this method is selected from the group consisting of allergic asthma, contact hypersensitivity, sunburn, UVB-induced skin damage, essential hypertension, cryopyrin-associated periodic syndromes (CAPS), Muckle-Wells syndrome (MWS), familial cold autoinflammatory syndromes (FCAS), neonatal onset multisystemic inflammatory disease/chronic infantile neurological cutaneous and articular syndrome (NOMD/CINCA), B-cell non-Hodgkin's lymphoma, acute myocardial infarction, myocardial infarction, allergic rhinitis, nasal polyposis, autoimmune encephalomyelitis (EAE), multiple sclerosis (MS), skin fibrosis in human systemic sclerosis (SSc), hyperhomocysteinemia (hHcys)-associated glomerular sclerosis, end-stage renal disease (ESRD), atherosclerosis, hepatic fibrosis, renal fibrosis, pulmonary fibrosis, chronic pulmonary fibrotic disorders, idiopathic pulmonary fibrosis (IPF), fibrotic lung disease, cystic fibrosis (CF), cardiac fibrosis, pancreatic islet fibrosis, chronic kidney disease (CKD), crystalline nephropathies, chronic obstructive pulmonary disease (COPD), ocular Bechet's disease, uvetitis, psoriasis, asbestosis, silicosis, malaria, Dengue, bacterial infection, allergic dermatitis, hyperoxic lung injury, conjunctivitis, keratitis, atopic dermatitis, psoriatic arthritis, vitiligo, Crohn's disease, metabolic syndromes linked with obesity, inflammation-associated cancers, hypersensitivity dermatitis, familial Mediterranean fever (FMF), familial Hibernian Fever (FHF), familial cold urticarial (FCU), pyogenic sterile arthritis, pyoderma gangrenosum, acne (PAPA), systemic onset juvenile arthritis, mevalonate kinase deficiency (MKD), Epidermolysis bullosa (EB), Epidermolytic ichthyosis (EI), and Schnitzler's syndrome (SS).

The invention also provides pharmaceutical compositions for the treatment of the disorders modulated by the described mechanisms. The pharmaceutical compositions of the invention comprise therapeutically effective amounts of diacerein or its analogs that are sufficient to achieve the purpose of the administration of these compositions. The pharmaceutical compositions of the invention can be in any suitable dosage form, including but not limited to tablets, oral solutions, injections, and other commonly used dosage forms.

When administered to a subject in need thereof, diacerein or its analogs can be prepared as a pharmaceutical composition. Pharmaceutical compositions contemplated for use for the purposes of the present invention can be in the form of a solid, solution, emulsion, dispersion, micelle, liposome and the like. The compositions may be administered using any means known in the art, such as intravenously, topically, intradermally, intramuscularly, transdermally, subcutaneously, intranasally, parenterally, intrathecally, vaginally, rectally, colorectally, orally, intracranially, retroorbitally, or intrasternally. Preferably, the compositions are adapted for oral administration. For example, the drug can be mixed with suitable excipients for the preparation of tablets, capsules, pellets, troches, lozenges, solutions, powders or granules, suspensions, hard or soft capsules and any other forms suitable for use.

In some embodiments, the subject is co-administered with one or more additional therapeutic agents suitable for the treatment of the relevant disorders selected from the group consisting of coagulation factor VIII, coagulation factor IX, acetaminophen, and nonsteroidal anti-inflammatory drugs (NSAIDs), including COX-2 inhibitors.

Examples of NSAIDs include, but are not limited to, 2-arylpropionic acids such as ibuprofen, ketorolac and naproxen; n-arylanthranilic acids such as mefenamic acid and meclofenamic acid; oxicams such as piroxicam and meloxicam; and arylalkanoic acids such as diclofenac, etodolac, indomethacin, and sulindac. Examples of COX-2 inhibitors include, but are not limited to, celecoxib, etoricoxib, rofecoxib, and vaidecoxib. Examples of coagulation factor VIII and factor IX include, but are not limited to, Hefixate, Monoclate-P, Beriate, BeneFix, Alprolix, Idelvion, and Rixubis.

In some embodiments, diacerein or its analogue can be the only active agent in the compositions of the invention. The compositions of the invention may contain pharmaceutical excipients (i.e., inactive compounds) commonly used in the art.

Suitable excipients include antioxidants, gelling agents, pH adjusting agents/buffers, penetration enhancers, preservatives, chelating agents, humectants, surfactants, emulsifiers, thickeners, solvents and stabilizers. Herein, excipients/ingredients in the present invention may have multiple functions, e.g., one excipient can be used as surfactant and/or stabilizer and/or emulsifier, etc.

Examples of antioxidants include, but not limited to, one or more of vitamin C, vitamin A and alpha-lipoic acid, ascorbyl palmitate, sodium pyrosulfite, butyl hydroxy anisole (BHA), butyl hydroxy toluene (BHT), and the like.

Suitable gelling agents may include, but not limited to, one or more of guar, xanthan, and carrenenan gums, anionic, nonionic, cationic and lipophilically modified guar gums, polyacrylic acids, polymethacrylic acids, cellulose resins, polyethylene glycols, hydroxy alkyl celluloses, carboxy alkyl celluloses, polyalkylene amines, and the like.

Examples of pH adjusting agents/buffers include, but not limited to, one or more of sodium bicarbonate, potassium bicarbonate, magnesium hydroxide, magnesium lactate, magnesium gluconate, aluminum hydroxide, aluminum hydroxide/sodium bicarbonate co precipitate, amino acids, aluminum glycinate, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, sodium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and the like.

Examples of penetration enhancers includes, but not limited to, one or more of diethylene glycol monoethyl ether, dimethyl sulfoxide, propylene glycol, isopropyl myristate (IPM), cal-cipotriene, detergents, emollients, Ethoxy diglycol, Triacetin, Propylene Glycol, Benzyl Alcohol, Sodium Laureth Sulfate, Dimethyl Isosorbide, Isopropyl Myristate, Medium Chain Triglyceride Oil (MCT Oil), Menthol, Isopropyl Palmitate, Isopropyl Isostearate, Propylene Glycol Monostearate, Lecithin, Diisopropyl Adipate, Diethyl Sebacate, Oleic Acid, Ethyl Oleate, Urea, Glyceryl Oleate, Caprylic/Capric Triglyceride, Propylene Glycol Dicaprylate/Dicaprate, Laureth 4, Oleth-2, Oleth-20, Propylene Carbonate, Nonoxynol-9, 2-n-nonyl-1,3-dioxolane, C7 to C14-hydrocarbyl substituted 1,3-dioxolane, 1,3-dioxane, or acetal, and Nonoxynol-15, and the like.

Preservatives can be, for instance, one or more of sodium benzoate, butylated hydroxy toluene, butylated hydroxyanisole, ethylenediamine tetraacetic acid, paraoxybenzoic acid esters, chlorobutanol, benzyl alcohol, phenylethyl alcohol, dehydroacetic acid, sorbic acid, benzalkonium chloride, benzethonium chloride, phenol, phenylmercuric nitrate, thimerosal, and/or propyl-paraben.

Examples of suitable solvents include, but not limited to, one or more of alcohol, castor oil, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, SD alcohol 40, triglycerides of saturated fatty acids, and the like.

Suitable stabilizers or surfactants can be, for example, one or more of ionic polysorbate surfactant, Tween 20, Tween 40, Tween 60, Tween 80, nonylphenol polyethylene glycol ethers, (alkyl phenol-hydroxypolyoxyethylene), Poly(oxy-1, 2-ethanediyl), alpha-(4-nonylphenol)-omega-hydroxy, branched (i.e., Tergitol® NP-40 Surfactant), nonylphenol polyethylene glycol ether mixtures (i.e., Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate, cetyl alcohol, stearic acid, polyoxyl stearate, and the like.

Even if an ingredient of the provided compositions may be an active agent in prior art formulations for purposes other than treatment of the relevant disorders mentioned above, it is still considered a pharmaceutical excipient for the purposes of the provided compositions as long as this ingredient is not present at an amount sufficient to effectively treat a relevant disorder.

Diacerein or its analogs and the additional therapeutic agents may be contained in a single formulation or may be co-administered as separate formulations.

Hereinafter, the present invention will be further illustrated with reference to the following examples. However, these examples are only provided for illustrative purposes; and not to limit the scope of the present invention.

EXAMPLE 1

Cell Culture

The 20 mg of rhein powder was dissolved in 1 mL 100% dimethyl sulfoxide (DMSO), sterilized by 0.22 µm pore filter membranes, and stored at −20° C. before use. The monosodium urate (MSU) crystal (10 mg/mL) was prepared in sterilized phosphate buffered saline (PBS). The adenosine 5%-triphosphate disodium salt (ATP) was dissolved in $ddH_2O$ and sterilized by 0.22 µm pore filter membranes. THP-1, human acute monocytic leukemia cell line (ATCC® TIB-202), were suspended in RPMI-1640 medium (GIBCO, Life Technologies, Grand Island, USA) supplemented with 10% fetal bovine serum and 1% of antibiotics (penicillin-streptomycin-amphotericin B) conditioned media. For macrophage-like differentiation, THP-1 cells were primed by 0.1 µM phorbol myristyl acetate (PMA) for 24 hours. Differentiated THP-1 cells were cultured with various dose of rhein treatment (0, 5 or 10 µg/mL) upon 100 µg/mL MSU stimulation for 6 hours. Culture supernatants and cell lysates were collected. For cell viability, PMA-primed THP-1 cells were detected in the presence or absence of rhein incubation for 24 hours by the Cell Counting Kit-8 (CCK-8 assay, Sigma-Aldrich, St Louis, USA). For cell adhesion test, the xCELLigence real-time cell analyzer system was performed according to the manufacturer's instructions.

Immunofluorescence Staining

PMA-primed THP-1 cells ($1\times10^6$ cells/mL) were cultured with 0, 5 or 10 µg/mL rhein overnight, and then stimulated by 100 µg/mL MSU crystals for 6 hours. Fluorescence confocal assay was performed to detect the human ASC and NLRP3 expression in paraformaldehyde-fixed THP-1 cells after treatment. Images were acquired with an Olympus FV1000 confocal microscope. The stained areas of ASC (green) and NLRP3 (red) staining distributions were quantified and analyzed by Metamorph analyzer. Merge of images with nuclear staining with DAPI shows colocalization of ASC with NLRP3 (yellow) (scale bars, 10 µm). The staining sections were normalized to PMA only group and shown as relative fold with the values for untreated control arbitrarily set to 1. Data were from one experiment with three fields (mean±SD). P-value was determined by the two-tailed unpaired t-test.

Results

Figure 2:
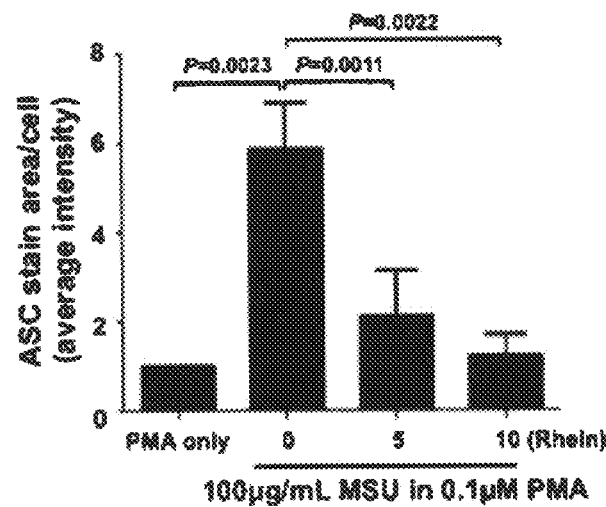
FIG. 2 is a statistical bar graph showing the ASC stain area after THP-1 cells were stimulated by MSU and treated with various dose of rhein.
Figure 3:
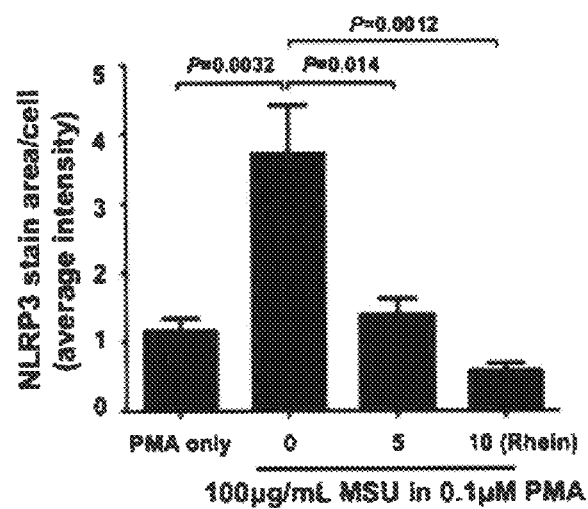
FIG. 3 is a statistical bar graph showing the NLRP3 stain area after cells were stimulated by MSU and treated with various dose of rhein.

During NLRP3 inflammasome activation, NLRP3 and ASC domains aggregate in the cell. Fluorescence confocal assay was used to measure NLRP3 and ASC protein levels in the MSU-stimulated THP-1 cells with rhein treatment, and the staining area was quantified. As shown in FIGS. 1 to 3, the immunofluorescence staining results showed that MSU crystals up-regulated the NLRP3 and ASC protein expressions (P=0.0023 and 0.0032, respectively). With rhein treatment, the staining of ASC sections significantly decreased about 64.0% and 79.0% average intensity of area/cell in a dose-dependent manner (P=0.0011 and 0.0022, respectively). In addition, rhein inhibited the NLRP3 levels about 62.5% and 84.1% average intensity of area/cell in the MSU-induced inflammation (P=0.014 and 0.0012, respectively).

This study showed that rhein suppressed the expression of ASC and NLRP3, thereby inhibiting the formation of ASC specks and NLRP3 inflammasome complex assembly.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for the treatment of a disorder selected from the group consisting of epidermolytic ichthyosis (EI), uvetitis and pulmonary fibrosis in a subject in need thereof, comprising administering to said subject a compound selected from the group consisting of diacerein, rhein, monoacetylrhein, salts, esters, and prodrugs thereof.

2. The method of claim 1, wherein the subject is a human.

3. The method of claim 1, wherein said disorder is epidermolytic ichthyosis (EI).

4. The method of claim 3, wherein the subject is a human.

5. The method of claim 1, wherein said disorder is uvetitis.

6. The method of claim 5, wherein the subject is a human.

7. The method of claim 1, wherein said disorder is pulmonary fibrosis.

8. The method of claim 7, wherein the subject is a human.

* * * * *